United States Patent [19]
Nelson

[11] Patent Number: 5,141,813
[45] Date of Patent: Aug. 25, 1992

[54] MULTIFUNCTIONAL CONTROLLED PORE GLASS REAGENT FOR SOLID PHASE OLIGONUCLEOTIDE SYNTHESIS

[75] Inventor: Paul S. Nelson, Union City, Calif.

[73] Assignee: Clontech Laboratories, Inc., Palo Alto, Calif.

[21] Appl. No.: 399,658

[22] Filed: Aug. 28, 1989

[51] Int. Cl.$^5$ .................. C07H 1/00; C07H 21/04; C03C 12/00; C07C 211/02
[52] U.S. Cl. .................. 428/402; 560/155; 536/27; 536/28; 536/29; 501/33
[58] Field of Search .......... 536/27, 28, 29, 23; 435/6; 501/33; 560/155; 428/402

[56] References Cited

PUBLICATIONS

Saili, R. K., S. Scharf, F. Faloona, K. B. Mullis, G. R. Horn, H. A. Erlich, and N. Arnheim (1985) "Enzymatic Amplification of β-glogin genomic sequences and restriction site analysis for diagnosis of sickle cell anemia", Science 230: 1350–1354.

Embury, S. H., S. J. Scharf, R. K. Saiki, M. A. Gholson, M. Golbus, N. Arnheim, and H. A. Erlich (1987) "Rapid prenatal diagnosis of sickle cell anemia by a new method of DNA analysis," N. Engl. J. Med. 316:656–660.

Liu, E., B. Hjelle, R. Morgan, F. Hecht, and J. M. Bishop (1987) "Mutations of the Kirsten- ras proto-oncogene in human preleukaemia," Nature 330:186–188.

Rodenhuis, S., M. L. van de Wetering, W. J. Mooi, S. G. Evers, N. van Zandwijk and J. L. Bos (1987) "Mutational activity of the K-ras oncogene," N. Engl. J. Med. 317:929–935.

Agrawal, S., C. Christondoulou, and M. J. Gait (1986) "Efficient methods for attaching non-radioactive labels to the 5' ends of synthetic ologodeozyribonucleotides," Nucl. Acids Res. 14:6227–6245.

Connolly, B. A. (1987) "The synthesis of oligonucleotides containing a primary amino group at the 5'-terminus," Nucl. Acid Res.15:3131–3139.

Jablonski, E., E. W. Moomaw, R. H. Tullis, and J. L. Ruth (1986) "Preparation of oligodeoxynucleotide-alkaline phosphatase conjugates and their use as hybridization probes," Nucl. Acids Res. 14:6115–6128.

Haralambidis, J., M. Chai, and G. W. Tregear (1987) "Preparation of base-modified nucleosides suitable for non-radioactive label attachment and their incorporation into synthetic oligodeoxyribonucleotides," Nucl. Acids Res. 15:4857–4876.

Li, P., P. P. Medon, D. C. Skingle, J. A. Lanser, and R. H. Symons (1987) "Enzyme-linked synthetic oligonucleotide probes: non-radioactive detection of enterotoxigenic Echerichia coli in faecal specimens," Nucl. Acid Res. 15:5275–5287.

Smith, L. M., S. Fung, M. W. Hunkapiller, T. J. Hunkapiller, L. E. Hood (1985) "The Synthesis of oligonucleotides containing an aliphatic amino group at the 5' terminus: synthesis of fluorescent DNA primers for use in DNA sequence analysis," Nucl. Acids Res. 13:2399–2412.

Sproat, B. S., B. Beijer, and P. Rider (1987) "The synthesis of protected 5'-mercapto-2', 5'-dideoxyribonucleoside-3'-O-phosphoramidites; uses of 5'-mercapto-oligodeoxyribonucleotides," Nucl. Acids Res. 15:4837–4848.

Ansorge, W., B. Sproat, J. Stegemann, C. Schwager, and M. Zenke (1987) "Automated DNA sequencing:

(List continued on next page.)

Primary Examiner—Johnnie R. Brown
Assistant Examiner—Gary L. Kunz
Attorney, Agent, or Firm—Saliwanchik & Saliwanchik

[57] ABSTRACT

The subject invention concerns a novel multifunctional solid support reagent which is useful in solid phase oligonucleotide synthesis. Specifically, the reagent is used in a solid phase oligonucleotide process to chemically modify the 3' terminus of a synthetic oligonucleotide with any chemical functional group. The invention reagent can be used to construct 3' labeled oligonucleotide hybridization probes to detect the presence of a target polynucleotide in biological and clinical samples.

2 Claims, 6 Drawing Sheets

OTHER PUBLICATIONS ultrasensitive detection of fluorecent bands during electrophoresis," Nucl. Acids Res. 15:4593-4602.

Sproat, B. S., B. Beijer, and P. Rider (1987) "The synthesis of protected 5'-dideoxyribonucleoside-3'-O-phosphoramidites; application of 5'-aminooligodeoxyribonucleotides," Nucl. Acids. Res. 15:6181-6196.

Sinha, N. D. and R. M. Cook (1988) "The preparation and application of functionalised synthetic oligonucleotides: III. Use of H-phosphonate derivatives of protected amino-hexanol and mercapto-propanol or -hexanol," Nucl. Acids Res. 16:2659-2669.

Lemaitre, M., B. Bayard, and B. Lebleu (1987) "Specific antiviral activity of a poly(L-lysine)-conjugated oligodeoxyribonucleotide sequences complimentary to vesicular somatitis virus N protein mRNA initiation site," Proc. Natl. Acad. Sci. USA 84:648-652.

Lemaitre, M., C. Bisbal, B. Bayard, and B. Lebleu (1987) "Biological activities of oligonucleotides linked to poly(L-lysine)," Nucleosides and Nucleotides 6:311-315.

Zuckerman, R., D. Corey, and P. Schultz (1987) "Efficient methods for attachment of thiol specific probes to the 3' ends of synthetic oligodeoxyribonucleotides," Nucl. Acids Res. 15:5305-5321.

MULTIFUNCTIONAL CONTROLLED PORE GLASS REAGENT FOR SOLID PHASE OLIGONUCLEOTIDE SYNTHESIS

BACKGROUND OF THE INVENTION

Single base substitutions in human genes are the cause or are strongly associated with a variety of human diseases such as the hemoglobinopathies (Saiki, R. K., S. Scharf, F. Faloona, K. B. Mullis, G. T. Horn, H. A. Erlich, and N. Arnheim [1985] Science 230:1350-1354; Embury, S. H., S. J. Scharf, R. K. Saiki, M. A. Gholson, M. Golbus, N. Arnheim, and H. A. Erlich [1987] N. Engl. J. Med. 316:656-660) and cancer (Liu, E., B. Hjelle, R. Morgan, F. Hecht, and J. M. Bishop [1987] Nature 330:186-188; Rodenhuis, S., M. L. van de Wetering, W. J. Mooi, S. G. Evers, N. van Zandwijk, and J. L. Bos [1987] N. Engl. J. Med. 317:929-935). Previously, if no convenient restriction sites were altered by the base change, then the only recourse has been to clone and sequence the affected gene. Recently, polymerase chain reaction (PCR) amplification of the DNA segment in question, coupled with hybridization of specific oligonucleotide probes, has allowed sequence determination without the need for molecular cloning. The applicability of the latter technique is dependent on the availability of versatile and inexpensive oligonucleotide probes.

Methods to covalently attach labels and reporter molecules to oligonucleotides have permitted their use as non-radioactive hybridization probes. New technologies in non-isotopic gene probes (Agrawal, S., C. Christodoulou, and M. J. Gait [1986] Nucl. Acids Res. 14:6227-6245; Connolly, B. A. [1987] Nucl. Acids Res. 15:3131-3139; Jablonski, E., E. W. Moomaw, R. H. Tullis, and J. L. Ruth [1986] Nucl. Acids Res. 14:6115-6128; Haralambidis, J., M. Chai, and G. W. Tregear [1987] Nucl. Acids Res. 15:4857-4876; Li, P., P. P. Medon, D. C. Skingle, J. A. Lanser, and R. H. Symons [1987] Nucl. Acids Res. 15:5275-5287), DNA sequencing analysis (Smith, L. M., S. Fung, M. W. Hunkapiller, T. J. Hunkapiller, and L. E. Hood [1985] Nucl. Acids Res. 13:2399-2412; Sproat, B. S., B. Beijer, P. Rider, and P. Neuner [1987] Nucl. Acids Res. 15:4837-4848; Ansorge, W., B. Sproat, J. Stegemann, C. Schwager, and M. Zenke [1987] Nucl. Acids Res. 15:4593-4602), electron microscopy (Sproat, B. S., B. Beijer, and P. Rider [1987] Nucl. Acids Res. 15:6181-6196), and X-ray crystallography (Sproat et al. [1987] Nucl. Acids Res. 15:4837-4848) have provided impetus for the development and improvement of such methods. As applications continue to emerge, more convenient oligonucleotide labeling techniques and reagents will be required.

Current methods to introduce chemical modifications into oligonucleotides employ special phosphoramidite reagents during solid phase synthesis. Attention has focused on the 5' terminus and a number of protected amino-alkyl phosphoramidites have been reported (Agrawal et al., supra; Connolly, supra; Jablonski et al., supra; Smith et al., supra; Sproat et al. [1987] Nucl. Acids Res. 15:6181-6196; Sinha, N. D. and R. M. Cook [1988] Nucl. Acids Res. 16:2659-2669) to incorporate a 5' terminal aliphatic primary amine. Oligonucleotides modified by these reagents can be subsequently derivatized with fluorophores, biotin, and other molecules. Similarly, phosphoramidite reagents have also been described which incorporate a thiol functionality on the 5' terminus (Sproat et al. [1987] Nucl. Acids Res. 15:4837-4848; Ansorge et al., supra; Connolly, B. A. [1985] Nucl. Acids Res. 13:4484-4502).

Techniques modifying the 3' terminus are inconvenient and tedious. Lemaitre et al. (Lemaitre, M., B. Bayard, and B. Lebleu [1987] Proc. Natl. Acad. Sci. USA 84:648-652; Lemaitre, M., C. Bisbal, B. Bayard, and B. Lebleu [1987] Nucleosides and Nucleotides 6:311-315) have described the attachment of a ribonucleoside to the 3' terminus of an oligonucleotide using T4 RNA ligase. Terminal 3' modification was achieved after periodate-oxidation of the ribose ring followed by reductive amination. Another procedure by Zuckerman et al. (Zuckerman, R., D. Corey, and P. Schultz [1987] Nucl. Acids Res. 15:5305-5321) incorporates a 3' terminal thiol group via solid phase oligonucleotide synthesis. Although this procedure is more efficient, it requires many synthetic steps and purifications. Thus, there remains a need for a simple and efficient method to synthesize 3' labeled oligonucleotides.

BRIEF SUMMARY OF THE INVENTION

The subject invention concerns a reagent for use in solid phase oligonucleotide synthesis having the following structure:

wherein:

C = carbon atom;

W = any solid such as controlled pore glass (CPG [CPG Biosupport, Inc., Fairfield, NJ]), alkylamine CPG, wherein alkyl can be from 1 to 50 carbon atoms, and isomeric forms thereof, any chemical modification of CPG, wherein the modification can be amines, hydroxyls, carboxyls, sulfhydryls, or disulfides, polystyrene and any solid support stable to all the conditions of solid phase oligonucleotide synthesis; W can also be a non-solid phosphoramidite group, $-OP(OR_3)NR_4R_5$, wherein $R_3 = -CH_3$, $-CH_2CH_2CN$, or alkane of 1 to 50 carbon atoms, inclusive, and isomeric forms thereof, and $R_4$, $R_5$ = methyl, ethyl, isopropyl, or alkane as defined above (if W is a non-solid phosphoramidite group it is not restricted to the 3' terminus);

X = a cleavable linking arm connecting carbon C to W which can be any combination of atom groups (e.g., $-(CH_2)_n-$, $-OCO-$, $-CO_2$, $-NHCO-$, $-CONH-$) that covalently connects to the solid phase (W) through a cleavable linkage, and is stable to all the conditions of solid phase oligonucleotide synthesis. Cleavable linkages include esters which are cleaved with ammonium hydroxide and disulfides which are cleaved with reducing agents. After oligonucleotide synthesis, cleavage of X from the solid phase results in the transfer of the entire multifunctional linking arm to the 3' terminus of the synthesized oligonucleotide. Preferably, $X = -O-CO-CH_2-CH_2-CO-$ (succinic acid) which is readily cleaved from the solid phase with ammonium hydroxide;

Y = a linking arm connecting carbon C to $R_1O-$ that is at least one carbon atom long and can be any combination of atom groups (e.g., $-(CH_2)_n-$, $-OCO-$, $-CO_2$, $-NHCO-$, $-CONH-$) that covalently connects to $OR_1$ and is stable to all the conditions of solid phase oligonucleotide synthesis;

Z = a linking arm connecting carbon C to $R_2$—A— that is at least one carbon atom long and can be any combination of atom groups (e.g., —$(CH_2)_n$—, —OCO—, —$CO_2$, —NHCO—, —CONH—) that convalently connects to $AR_2$ and is stable to all the conditions of solid phase oligonucleotide synthesis;

$R_1O$ = a protected hydroxide group where $R_1$ is a base stable-acid labile hydroxyl protecting group, e.g., $R_1$ can be monomethoxytrityl (MMT) or dimethoxytrityl (DMT);

A = —NH—, —S—, or any functional group that is capable of attaching a reporter molecule or any detectable complex;

$R_2$ = corresponding protecting group for A that is stable to all the conditions of solid phase oligonucleotide synthesis; and B = H, —$CH_3$, —Z—A—$R_2$, —Y—$OR_1$, or any combination of atom groups that are inert to solid phase oligonucleotide synthesis.

Specifically exemplified herein is MF-CPG ® (3' Amine-ON CPG) wherein, with reference to (I) above, W = long chain alkyl amine CPG; X = —O—CO—$CH_2$—CO—; B = H; Y = —$CH_2$—; Z = —$CH_2$—; A = —NH—; $R_2$ = 9-fluorenylmethyl (Fmoc), trifluoroacetyl (TFA), or any base labile-acid stable amine protecting group; and $R_1$ = DMT.

The structure of MF-CPG ® (3' Amine-ON CPG) is as follows:

wherein the alkyl of alkylamine can be from 1 to 50 carbon atoms, inclusive, and isomeric forms thereof.

The subject invention is useful in solid phase oligonucleotide synthesis (both oligodeoxyribonucleotide and oligonucleotide) to chemically modify the 3' terminus of a synthetic oligonucleotide with any chemical functional group. Useful functional groups are primary amines, sulfhydryls, disulfides, and any other group typically used for conjugation of reporter molecules. Also, the subject invention can be used for attaching a label to a functional group introduced at the 3' terminus of a synthetic oligonucleotide. Labels include any reporter molecules such as biotin, haptens, fluorophores, proteins, enzymes, and antibodies. Such modified and labeled oligonucleotide probes can be used in any application where the said probe hybridizes to complementary sequences of a target polynucleotide. Further, the invention can be used for detecting low copy genes by using the polymerase chain reaction (PCR) to amplify the target gene segment and then employing the invention for detecting the presence of specific polynucleotide in samples containing the same, biological samples, and, for example, clinical samples such as serum and blood. Still further, the subject invention can be used for the diagnosis of infectious diseases and pathogens, detection of oncogenes, diagnosis of genetic disorders, and detection of point mutations or single base substitutions. The subject invention has utility in the areas of anti-sense molecular biology, electron microscopy, X-ray crystallography, and site-specific cleavage of DNA.

Thus, the subject invention concerns a novel multifunctional controlled pore glass reagent (MF-CPG ®) (FIG. 1), useful to incorporate 3' terminal primary aliphatic amines into synthetic oligonucleotides. MF-CPG ® comprises a unique succinic acid linking arm which possesses both a masked primary amine for label attachment and a dimethoxytrityl protected hydroxyl for nucleotide chain elongation. Using MF-CPG ®, a simple and convenient technique has been devised to attach non-radioactive labels to the 3' terminus of oligonucleotides. Bifunctional probes can then be constructed by $^{32}P$ labeling the 5' terminus with T4 kinase and gamma $^{32}P$-ATP. Using such bifunctional oligonucleotide probes in conjunction with PCR amplification, a person can detect a single base substitution in a target DNA segment. Exemplified herein is the detection of a single base substitution of the human H-ras protooncogene employing either functionality. The invention technique thus expands the potential applications for oligonucleotides as hybridization probes.

DETAILED DISCLOSURE OF THE INVENTION

Materials and Methods

Long chain alkylamine CPG was purchased from Pierce Chemical Co. Biotin-XX-NHS ester, PCR amplimers, and the Gene-tect Non-Isotopic Detection System were obtained from Clontech Laboratories, Inc. Taq polymerase was acquired from Perkin Elmer Cetus. HPLC was performed on a Rainin Rabbit HPX System using aquapore C8 reverse phase columns (Applied Biosystems, Inc.) for both preparative (100 × 10 mm) and analytical (30 × 4.6 mm) runs. A Biosearch Cyclone DNA synthesizer was used for oligonucleotide synthesis.

The subject invention comprises a novel and simple method to synthesize 3' oligonucleotides. In conventional solid phase DNA synthesis, the 3' terminal nucleotide is pre-attached to the CPG support from the 3' hydroxyl through a succinimic acid linking arm, and the oligonucleotide is synthesized from the 5' hydroxyl repetitive cycles of chemical reactions. In the subject invention, a 3' primary aliphatic amine replaces the pre-attached nucleoside with a unique multifunctional linking arm to give a multifunctional CPG, MF-CPG ® (FIG. 1) which transfers a primary amine to the 3' terminus of a synthesized oligonucleotide without changing any chemistry or adding extra steps. MF-CPG ® possesses a uniquely engineered linking arm that complies with four important criteria. First, the linking arm is attached to the CPG through an ester functionality that is readily cleaved with ammonium hydroxide treatment. Second, the linking arm contains a masked primary aliphatic amine which is acid stable and resistant to all the reagents used in normal oligonucleotide synthesis. Third, in addition to being acid stable, the amine protecting group is readily removed with ammonium hydroxide treatment. Fourth, the linking arm contains a dimethoxytrityl protected primary hydroxyl group for oligonucleotide chain elongation. Hence, the method is fully adaptable to commercial DNA synthesizers and is as easy as synthesizing normal oligonucleotides.

Since a reporter molecule now can be easily attached to the 3' terminus of any oligonucleotide, both the 5' and 3' termini can be used to label the oligonucleotide. Such bifunctional oligonucleotide probes are both sensitive and specific in detecting single base substitutions in target DNA when used in conjunction with PCR. The sensitivity and specificity are the same regardless of the detection system; autoradiography or colorimetric detection with a streptavidin-alkaline phosphatase conjugate. The convenience of using MF-CPG ® to non-isotopically label an oligonucleotide at the 3' terminus with subsequent $^{32}$P labeling at the 5' terminus makes this reagent an attractive alternative to current methods of functionalizing oligonucleotides. Thus, the invention technique expands the potential for applications employing functionalized oligonucleotides.

Figure 1:
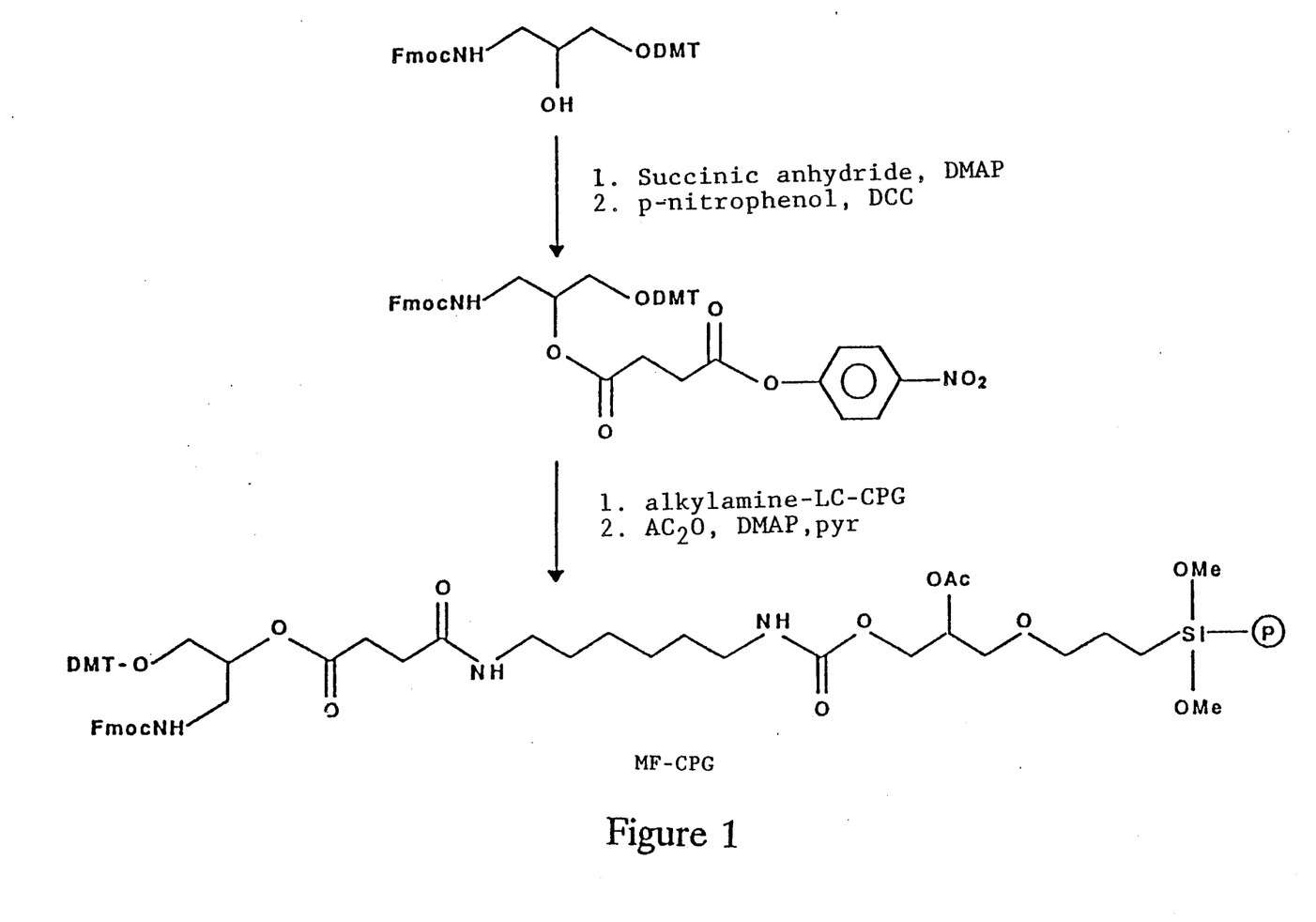
FIG. 1: The synthetic scheme for MF-CPG ®.

The preparation of MF-CPG ® is outlined in FIG. 1. N-Fmoc-O-DMT-3-amino-1,2-propanediol was first derivatized with succinic anhydride. The carboxyl group of the succinylated derivative was converted to a p-nitrophenyl ester and directly reacted with long chain alkylamine CPG to give MF-CPG ®. After capping, the loading capacity of MF-CPG ® was determined to be 27.8 μmol/g.

Figure 2A:
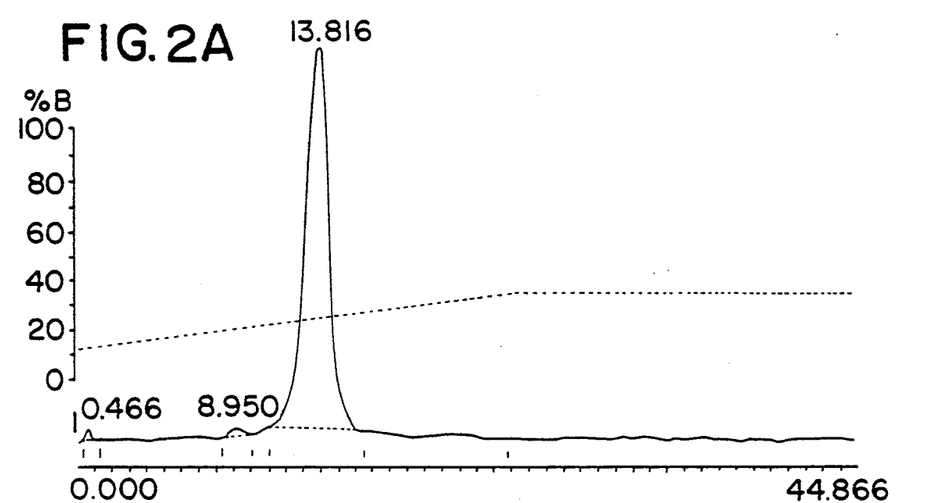
FIG. 2: Analytical chromatograms of purified 3' biotinylated H-ras oligonucleotide probes.
Figure 2B:
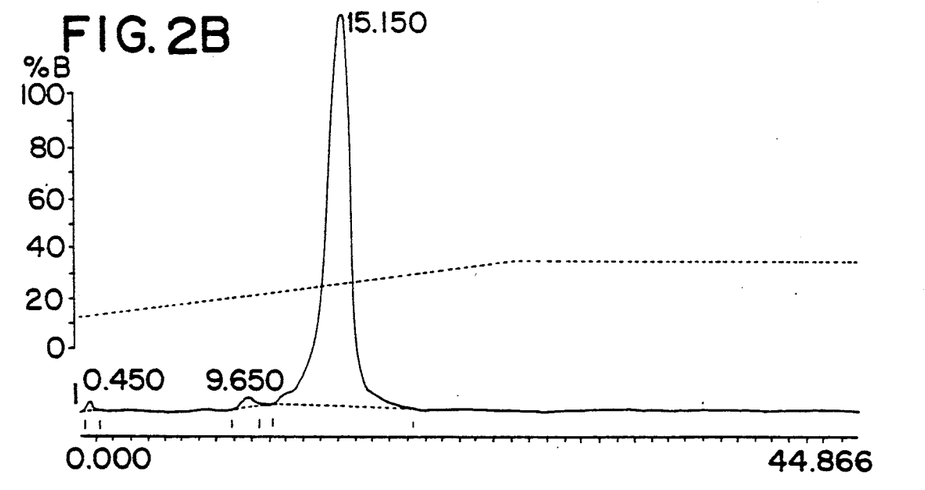

Two bifunctional oligonucleotide probes were constructed using MF-CPG ® as follows: First, two 3' amino-modified oligonucleotides, GGCGCCGGCGGTGTGGGCAA-X (H-ras, wild type) and GGCGCCGGCGATGTGGGCAA-X (H-ras, codon 13 Asp) [X=3' primary amine modification], were synthesized using MP-CPG. The coupling efficiency of the first nucleotide, which is indicative of 3' primary amine incorporation, was >97% in both cases. After standard cleavage and deprotection with ammonium hydroxide, the crude 3' amino-modified oligonucleotides were biotinylated with Biotin-XX-NHS ester. The long linking arm of Biotin-XX-NHS ester, a 14 atom spacer (XX) consisting of two e-aminocaproic acid moieties linked in series, was used to make the biotins more available for detection. After size exclusion on Sephadex G-25 (Pharmacia), the biotinylated oligonucleotides were purified by preparative HPLC on a C8 reverse phase column. Analytical HPLC chromatograms are shown in FIG. 2. The presence of biotin was confirmed by a p-methylamino-cinnamaldehyde colorimetric test. Finally, the construction of the bifunctional probes was completed by $^{32}$P labeling of the 5' ends with T4 kinase and gamma $^{32}$P-ATP.

Figure 3A:
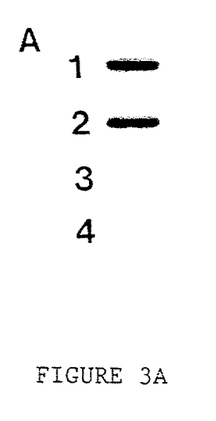
FIG. 3: Detection of point mutations in the human H-ras gene using specific bifunctional oligonucleotide probes.
Figure 3B:
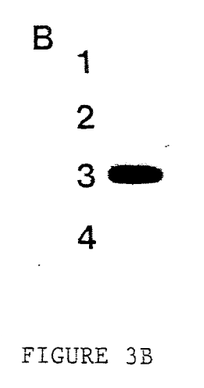

The applicability of these bifunctional oligonucleotide probes was assessed in detecting single base substitutions in the H-ras protooncogene. The probes used were specific either for the wild type H-ras sequence at condon 3 (GGT) or for the transforming mutant sequence at codon 13 (GAT) which substitutes aspartate for glycine. A 110-base pair segment which includes codon 13 f the H-ras gene was amplified from genomic DNA using the polymerase (PCR). By autoradiography (FIG. 3B), the condon 13 aspartate probe hybridized only with the amplified DNA carrying the H-ras codon 13 aspartate mutation and not with DNA from normal placenta, a transformed mouse fibroblast cell line (NIH3T3) harboring a mutant human H-ras gene with a codon 12 valine substitution (GTT), or with placental DNA amplified in the region surround N-ras codons 12 and 13. Hybridization with the wild type codon 13 H-ras probe (FIG. 3A), however, showed a signal only with amplified DNA from normal placenta and the NIH3T3 cell line whose murine H-ras gene can also be amplified using our current amplimers. Cross hybridization between the human and mouse wild type H-ras genes was unexpected but may indicate that the sequences probed are identical in the two species.

Figure 3C:
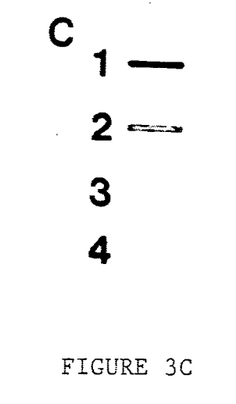
Figure 3D:
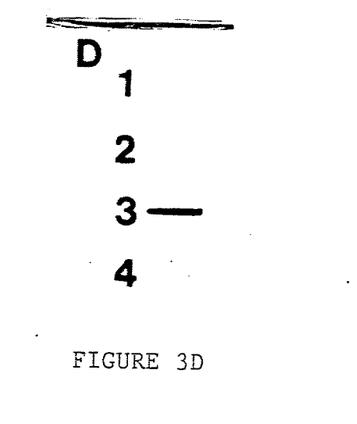

When the same hybridized filters were incubated with streptavidin-alkaline phosphatase and 5-bromo-4-chloro-3-indolyl-phosphate (BCIP), colorimetric signals were seen over the same slots exhibiting a radiographic signal (FIG. 3C and 3D). Thus, when used in conjunction with PCR, these bifunctional probes are both sensitive and specific in detecting single base pair mismatches in target DNA. Furthermore, an oligonucleotide probe from a single MF-CPG ® preparation can be either biotinylated or radiolabeled without compromising hybridization sensitivity.

Following are examples which illustrate procedures, including the best mode, for practicing the invention. These examples should not be construed as limiting. All percentages are by weight and all solvent mixture proportions are by volume unless otherwise noted.

EXAMPLE 1

Preparation of MF-CPG ®

To a solution of N-Fmoc-O-DMT-3-amino-1,2-propanediol (2.2 g, 3.5 mmol) and 4-dimethylaminopyridine (200 mg, 0.9 mmol) in anhydrous pyridine (12 ml) was added succinic anhydride (300 mg, 3 mmol). The reaction was stirred at room temperature for 17 hours. The consumption of starting material was followed by TLC using methanol-dichloromethane (1:49) as the mobile phase. The mixture was diluted in ethyl acetate (100 ml), washed with 0.5M sodium chloride (3×100 ml) and saturated sodium chloride (1×100 ml), and dried over anhydrous sodium sulfate. After concentrating by rotary evaporation and drying under high vacuum (45° C.), 1.74 g of a yellow solid was obtained.

The yellow solid was dissolved in dry dioxane (10 ml) containing anhydrous pyridine (0.5 ml) and p-nitrophenol (350 mg, 2.5 mmol). Dicyclohexylcarbodiimide (1.0 g, 4.8 mmol) was added and the mixture was stirred at ambient temperature. After a few minutes, dicyclohexylurea began to precipitate. The reaction was monitored by TLC (methanol-dichloromethane, 1:9) and after 3 hours, the dicyclohexylurea was collected by filtration. Long chain alkylamine CPG (5.0 g) was suspended in the filtrate containing the p-nitrophenyl ester derivative, triethylamine (1.0 ml) was added, and the mixture was shaken overnight at room temperature. The derivatized support was copiously washed with dimethylformamide, methanol, and diethyl ester and dried in vacuo. Before capping the unreacted alkylamine groups, the loading capacity of the MF-CPG ® was assayed by determining the amount of dimethoxytrityl cation released upon treatment with perchloric acid according to published procedures (*Oligonucleotide Synthesis: A Practical Approach*, M. J. Gait (ed.), IRL Press, Oxford, 1984).

Finally, capping of MF-CPG ® was achieved by treatment with acetic anhydride-pyridine-DMAP (10:90:1. v/v/w) for one hour. The support was thoroughly washed with methanol and diethyl ether and dried under high vacuum to give 4.95 g of MF-CPG ®. The capped MF-CPG ® gave a negative ninhydrin test (Smith et al., supra).

3' Amine-ON ™ CPG, prepared by the above process, has the following structural formula:

EXAMPLE 2
Synthesis of 3' Biotinylated Oligonucleotide Probes

Two 3' amino-modified oligonucleotides, GGCGCCGGCGGTGTGGGCAA-X (H-ras, wild type) and GGCGCCGGCGATGTGGGCAA-X (H-ras, codon 13 Asp) [X=3' primary amine modification], were synthesized using MP-CPG on a Biosearch Cyclone DNA synthesizer. Standard columns were packed with 1 μmol of MF-CPG ® and DNA synthesis was performed by suggested manufacturer protocols without any program changes. The coupling efficiency of the first nucleotide was determined by measuring the deprotected dimethoxytrityl cation concentration. Solid support cleavage and deprotection were accomplished with concentrated ammonium hydroxide.

Each crude amino-modified oligonucleotide was dissolved in 0.8 ml of 0.1M NaHCO$_3$/NaCO$_3$ (pH 9). Biotin-XX-NHS ester in dimethylformamide (100 mg/ml, 0.25 ml) was added and the mixture as allowed to react for 16 hours at room temperature. The biotinylated probes were purified on Sephadex G-25 columns (1×40 cm) and then by preparative HPLC. Analytical HPLC chromatograms of the purified 3' biotinylated probes are shown in FIG. 2. The presence of biotin was confirmed by a p-methylaminocinnamaldehyde colorimetric test.

EXAMPLE 3
$^{32}$P 5' End Labeling of the Biotinylated Oligonucleotide Probes The H-ras biotinylated probes were $^{32}$P 5' end labeled using a modification of the method described by Berent et al. (Berent, S. L., M. Mahmoudi, R. M. Torczynski, P. W. Bragg, and A. P. Bollon [1985] BioTechniques 3:208–220). 100 ng of the oligonucleotide probe were dissolved in 30 μl of distilled water and heated to 65° C. for 3 minutes. The oligomers were then taken up to 50 μl of a reaction buffer which contained 50 mM Tris-HCl (pH 7.5), 10 mM MgCl$_2$, 5 μM DTT, 0.1 mM spermidine, 10 μl gamma $^{32}$P-ATP (specific activity 6000 Ci/mM), and 15–20 units of T4 kinase. This reaction mixture was incubated at 37° C. for 30 minutes followed by the addition of another 15–30 units of kinase and further incubation for 30 minutes. The labeled probe was then isolated using a G-25 Sephadex column.

EXAMPLE 4
PCR Amplification of the H-ras Protooncogenes

Amplification of genomic DNA by the polymerase chain reaction (PCR) has been previously described (Liu et al., supra; Saiki et al., supra). Two different sets of amplifying primers (amplimers) were used to amplify specific ras oncogene segments of genomic DNA. ATGACGGAATATAAGCTGGT (5' H-ras amplimer) and CTCTATAGTGGGGTCGTATT (3' H-ras amplimer) were used to amplify the region around codons 12 and 13 of the H-ras gene; A T G A C T G A G T A C A A A C T G G T (5' N-ras amplimer) and CTCTATGGTGGGATCATATT (3' N-ras amplimer) were used to amplify the same codon region of the N-ras gene. 1 μg of genomic DNA was amplified in a 100 μl volume containing 50 mM KCl, 10 mM Tris (pH 8.3), 1.5 mM MgCl$_2$, 0.1 gelatin, 0.5 mM all four dNTPs, and 2.5 units Taq polymerase. The first amplification cycle included denaturation at 95° C. for 5 minutes, annealing at 55° C. for 2 minutes, and primer extension at 68° C. for 2 minutes. The remaining 35 cycles were performed with 2 minute incubation periods at each temperature.

The generation of target DNA with an H-ras codon 13 Asp mutation was accomplished by the method described in Rochlitz et al. (Rochlitz, C. F., G. K. Scott, J. M. Dodson, and C. C. Benz [1988] DNA 7:515–519). In this reaction, the sequence of the 3' amplifying oligomer has been noted above. The 5' amplimer, however, encompasses the 20 nucleotide sequence at condon 12 and 13 of H-ras and contains a point mutation encoding a glycine to aspartate change in condon 13 (GGCGCCGGCGATGTGGGCAA). DNA generated through PCR amplification was used as target DNA in oligonucleotide hybridization analysis. In this manner, the amplified DNA incorporates the oligonucleotide with the codon 13 aspartate mutation.

EXAMPLE 5
Hybridization of Probe and Post Hybridization Washes with Tetramethylammonium Chloride (TMAC)

40 μl of the amplifed samples were added to 80 μl of 0.4N NaOH, and heated to 95° C. for 2 minutes. The reaction mixtures were neutralized with 100 μl of 2M Tris-HCl (pH 7.4), and the solution slotted onto Amersham Hybond nylon filter. The DNA was crosslinked onto the filter by UV radiation under conditions suggested by the manufacturer.

The slot blots were pre-hybridized for 2 hours at 37° C. with 10–15 mls of 5X SSPE, 5X Denhardt's, 0.5% SDS, and 100 mM sodium pyrophosphate (pH 7.5). A labeled probe was then added to this solution to a final concentration of 5×10$^6$ cpm/ml and the filters were hybridized at 50° C. for 4 to 12 hours. Following this incubation, the filters were washed once at room temperature with 6X SSC for 20 minutes, and twice at 61° C. in 3M TMAC, 50 mM Tris-HCl (pH 8), 2 mM EDTA, and 0.1% SDS. The filters were then washed once at room temperature with 6X SSC. Hybridization was detected both by autoradiography, and by colorimetric detection with a streptavidin-alkaline phosphatase conjugate (Clontech's Gene-tect System) on the same slot blot.

EXAMPLE 6
Preparation of Non-Isotopic Oligonucleotide Labeling Kits (NIO-Label ™ Kits)

3' non-isotopic oligonucleotide (NIO) labeling kits are complete kits designed to conveniently label synthetic oligonucleotides at the 3' terminus with either biotin or fluorescein. The labeling process is divided into two procedures which are outlined in Sequence 1. First, an oligonucleotide is functionalized with a primary aliphatic amine at its 3' terminus using 3' Amine-ON CPG (Sequence 2). 3' Amine-ON CPG is a unique CPG that incorporates a primary amine on the 3' terminus of an oligonucleotide. It is fully compatible with automated DNA synthesizers. Secondly, the 3' amino-modified oligonucleotide is reacted with Biotin-XX-NHS ester or FITC. All buffers and reagents are supplied for this labeling procedure. Biotin-XX-NHS ester is a unique product, having an extra long linking arm (XX) consisting of 14 atoms (Sequence 3).

List of Components 1. 3' Amine-ON CPG, four 1 μmol columns (Clontech Catalog No. 5220-1; Clontech Laboratories, Inc., Palo Alto, CA).
2. Biotin-XX-NHS ester, 100 mg (Clontech Catalog No. K1072-1) or FITC, 100 mg (Clontech Catalog No. K1073-1).
3. 10X labeling buffer, 1.0M sodium bicarbonate/carbonate (pH 9) 0.5 ml.
4. N,N-Dimethylformamide, 1.0 ml.

Sequence 1.
Scheme for non-isotopic oligonucleotide labeling with CLONTECH's NIO-Label Kits, using 3' Amine-ON CPG Method Modifying the 3' terminus with a primary aliphatic amine

1. Attach a 3' Amine-ON to your automated DNA synthesizer.
2. Enter the oligonucleotide sequence you wish to synthesize. Make sure you enter the 3' terminal base of your sequence as the 2nd base from the 3' end. Note that 3' Amine-ON CPG has a bifunctional linking arm attached to it instead of the 3' terminal base. Hence, the 3' base is not on the CPG as with normal oligonucleotide synthesis. This must be accounted for when you enter the sequence. Since automated synthesizers assume that the 3' base is attached to the CPG, a nonsense base must be entered at the 3' terminus when using 3' Amine-ON CPG.
3. Initiate the synthesis using the Trityl-Off mode, i.e., remove the final DMT protecting group. If desired, the primary amine incorporation can be determined by measuring the deprotected dimethoxytrityl concentration of the first coupling cycle, typically >95%.

Deprotection

4. Cleave the 3' amino-modified oligonucleotide from the CPG by treating it with 1 ml of ammonium hydroxide at room temperature for 2 hours. It is convenient to use luer tip syringes for this step. Be careful not to let the ammonia evaporate.
5. Complete the deprotection by transferring the ammonium hydroxide solution to a 1.5 ml screw cap microcentrifuge tube and heat at 55° C. for 6 hours to overnight. Evaporate to dryness by vacuum centrifugation or rotary evaporation (Caution: ammonia gas builds up at 55° C.; cool to 4° C. before opening the screw cap microcentrifuge tube). The 3' amino-modified oligonucleotide is now ready for labeling. As an option, you may wish to quantitate the primary amine groups by a published procedure (Smith et al. [1985] supra).

Labeling (Agrawal, S. et al. [1986] Nucl. Acids Res. 14:6227–6245)

6. The following reaction is designed for a 1 μmol synthesis. In a 1.5 ml microcentrifuge tube, dissolve the total crude 3' amino-modified oligonucleotide (from step 5) in 900 μl deionized water.

7. Add 100μ of 10X labeling buffer.
8. Biotin labeling (Clontech Cat. No. K1072-1): Add 250 μl of a freshly prepared Biotin-XX-NHS ester in N,N-dimethylformamide (DMF). Prepare immediately before use by dissolving 25 mg of Biotin-XX-NHS ester in 250 μl DMF. Vortex immediately after addition. FITC labeling (Clontech Cat. No. K1073-1): Same procedure as biotin labeling except replace 25 mg Biotin-XX-NHS ester with 25 mg of FITC.
9. Incubate at room temperature overnight. When using FITC, perform the reaction in the dark. If precipitation occurs, incubate at 42° C. for 2 hours.
10. Pass the reaction mixture down a 1.0 cm×40 cm column of Sephadex (Pharmacia) G25 or G50. The Sephadex column should be saturated first by passing 1 mg of sheared, denatured salmon sperm DNA through and washing with 100 ml of deionized water. Load sample from step 10 and elute with deionized water. The labeled oligonucleotide will elute in the void volume. Collect 1 ml fractions; monitor separation via UV absorption at 260 nm.

Purification

In many applications, further purification may not be necessary. However, to achieve optimum results, it is recommended to purify by RP-HPLC or electrophoresis.

Reverse phase HPLC. The lipophilic character of both biotin and fluorescein aid in oligonucleotide purification by RP-HPLC. The biotin or fluorescein labeled oligonucleotide is retained longer on the column requiring a higher acetonitrile concentration to elute. Thus, as the last peak to elute, it is easily separated.

Use a RP-C18 analytical column (4.6 mm×250 mm). Set detector wavelength to 260 nm. Use the following gradient system as a reference run: A=0.1M triethylammonium acetate (pH 7), B=50% acetonitrile in 0.1M triethylammonium acetate (pH 7); 20-80% B, 60 minutes; 1.0 ml/minute. Since retention time will vary with the size of the oligonucleotide, you may wish to adjust the gradient after the first run.

Polyacrylamide gel electrophoresis (PAGE). Use conventional PAGE methods for separation of oligonucleotides, employing a 1.5 mm thick denaturing (urea) polyacrylamide gel. The percentage of acrylamide and bis-acrylamide will depend on the size of the oligonucleotide synthesized. Load 1-2 OD labeled oligonucleotide per well.

After electrophoresis, the labeled oligonucleotide may be visualized as follows: Remove the glass plates from the gel and wrap it in transparent plastic wrap. In a darkroom, place the gel on a fluorescent TLC plate and use a UV lamp to observe fluorescent quenching. The labeled oligonucleotide runs the slowest, since it has the highest molecular weight, and is therefore easily identified (Warning: excessive exposure to UV light may cause crosslinking of the DNA). Excise the labeled oligonucleotide with a razor blade. Crush the gel in a test tube and incubate in 0.1M ammonium bicarbonate at room temperature overnight. Finally, desalt the oligonucleotide by passing it through a Sephadex G25 column.

Confirmation of Label

Biotin (Clontech Cat. No. K1070-1): The presence of biotin can be determined by a p-dimethylaminocinnamaldehyde colorimetric test (McCormick, C. B. and J. A. Roth [1970] Methods Enzymol. 18:383-385). Spot 5 μl of a 30-40 OD/ml solution of the biotinylated oligonucleotide on a silica gel TLC plate. Spray with a solution of 0.2% p-dimethylaminocinnamaldehyde, 2% sulfuric acid in ethanol. Develop by slight heating. The presence of biotin is visualized by a pink-red spot.

Fluorescein (Clontech Cat. No. K1071-1): The presence of fluorescein is easily determined by its absorption maximum at 495 nm (Smith, L. M. et al. [1985], supra). Dilute an aliquot of the FITC-labeled oligonucleotide to approximately 1.0 OD/ml (pH 7.5). Assay for the presence of fluorescein by measuring absorbance in the range of 400-600 nm; an absorbance maximum should be observed between 490 and 500 nm.

I claim:

1. A compound having the following structure:

wherein W is alkylamine controlled pore glass, wherein said alkylamine has 1 to 50 carbon atoms.

2. A non-isotopic oligonucleotide labeling kit comprising the following separately compartmentalized components:
   (a) a composition comprising a compound having the following structure:

wherein W is alkylamine controlled pore glass, wherein said alkylamine has 1 to 50 carbons; and
   (b) an appropriate reporter molecule selected from the group consisting of biotin and fluorescein.

* * * * *

UNITED STATES PATENT AND TRADEMARK OFFICE
CERTIFICATE OF CORRECTION

PATENT NO.    :   5,141,813

DATED         :   August 25, 1992

INVENTOR(S)   :   Paul S. Nelson

It is certified that error appears in the above-identified patent and that said Letters Patent is hereby corrected as shown below:

Column 3:   line 24: "X = –O–CO–CH$_2$–CO–" should read --X = –O–CO–CH$_2$–CH$_2$–CO--.

Column 4:   line 45: "3'" should read --3' labeled--; line 50: "repetitive" should read --by repetitive--.

Column 5:   line 55: "codon 3 (GGT)" should read --codon 13 (GGT)--; line 58: "13f" should read --13 of--.

Column 8:   line 14: "Rochilitz" should read --Rochlitz--.

Column 9:   line 12: "or" should read -- -or- --.

Signed and Sealed this

Ninth Day of November, 1993

Attest:

BRUCE LEHMAN

*Attesting Officer*    *Commissioner of Patents and Trademarks*